US006928142B2

(12) United States Patent
Shao et al.

(10) Patent No.: US 6,928,142 B2
(45) Date of Patent: Aug. 9, 2005

(54) NON-INVASIVE PLAQUE DETECTION USING COMBINED NUCLEAR MEDICINE AND X-RAY SYSTEM

(75) Inventors: Lingxiong Shao, Saratoga, CA (US); Chuanyong Bai, Mountain View, CA (US); Mary K. Durbin, San Jose, CA (US)

(73) Assignee: Koninklijke Philips Electronics N.V., Eindhoven (NL)

( * ) Notice: Subject to any disclaimer, the term of this patent is extended or adjusted under 35 U.S.C. 154(b) by 186 days.

(21) Appl. No.: 10/274,353

(22) Filed: Oct. 18, 2002

(65) Prior Publication Data

US 2004/0076262 A1 Apr. 22, 2004

(51) Int. Cl.[7] .................. G01N 23/04; G01T 1/161; A61B 5/05
(52) U.S. Cl. .................. 378/63; 378/197; 378/205; 250/363.04; 600/407; 600/425; 600/436
(58) Field of Search ........................... 378/62, 63, 195, 378/196, 197, 205, 206, 207; 250/363.04; 600/407, 425, 427, 429, 436

(56) References Cited

U.S. PATENT DOCUMENTS

| | | | | |
|---|---|---|---|---|
| 3,863,623 | A | * | 2/1975 | Trueblood et al. .......... 600/431 |
| 5,409,001 | A | * | 4/1995 | Seyler et al. ............... 600/427 |
| 5,452,721 | A | * | 9/1995 | Hacker ....................... 600/436 |
| 5,813,985 | A | | 9/1998 | Carroll |
| 5,822,814 | A | | 10/1998 | Van der Ende |
| 5,838,758 | A | * | 11/1998 | Krug et al. .................... 378/53 |
| 6,031,888 | A | | 2/2000 | Ivan et al. |
| 6,114,702 | A | * | 9/2000 | Doerfel ....................... 250/366 |
| 6,205,347 | B1 | | 3/2001 | Morgan et al. |
| 6,364,526 | B2 | | 4/2002 | Ivan et al. |
| 6,375,925 | B1 | | 4/2002 | Tsimikas et al. |
| 6,379,043 | B1 | | 4/2002 | Zylka et al. |
| 6,459,925 | B1 | | 10/2002 | Nields et al. |
| 6,490,476 | B1 | * | 12/2002 | Townsend et al. .......... 600/427 |
| 6,533,455 | B2 | * | 3/2003 | Graumann et al. ......... 378/205 |
| 2003/0147489 | A1 | * | 8/2003 | Bijjani et al. .................. 378/4 |
| 2003/0212320 | A1 | * | 11/2003 | Wilk et al. .................. 600/407 |

FOREIGN PATENT DOCUMENTS

WO WO 00/75691 A1 12/2000

OTHER PUBLICATIONS

Bergman, Alanah, et al; Technique to Obtain Positron Emission Mammography Images in Registration with X–Ray Mammograms; Med. Phys. 25 (11),Nov. 1998, pp 2119–2129.

* cited by examiner

Primary Examiner—Allen C. Ho (57) ABSTRACT

A diagnostic imaging system (20) comprising a computer workstation (26) for controlling the imaging system, interfacing with an operator and generating images. A coordinate system (100) is in data communication with the computer workstation. The coordinate system (100) is adapted to describe relative position of components in the diagnostic imaging system (20). A subject support (30) is describable within the coordinate system and an X-ray sub-system (22) is positionable around the subject support (30). Position sensors (44a) are operatively connected to the x-ray sub-system (22) and they provide signals to the workstation (26) indicative of the position of components of the x-ray sub-system (22) within the space represented by the coordinate system. A nuclear camera sub-system (24) is positionable around the subject support (30). Position sensors (44b) are operatively connected to the nuclear camera sub-system (24) and provide signals to the workstation (26) indicative of position of components of the nuclear camera sub-system within the coordinate system. The workstation (100) includes a region of interest position determination function (108) for determining the position within the imaging system of a region of interest (40) in an image generated by the x-ray sub-system (22). The region of interest (40) is precisely targeted using the control console (26) for imaging by the nuclear camera (50).

19 Claims, 5 Drawing Sheets

NON-INVASIVE PLAQUE DETECTION USING COMBINED NUCLEAR MEDICINE AND X-RAY SYSTEM

BACKGROUND

The present invention relates to an apparatus and method for detection of plaque and is related to an apparatus and method that is useful to non-invasively locate and identify vulnerable plaque. The present invention finds application in conjunction with a diagnostic imaging system having a nuclear diagnostic imaging sub-system in combination with an x-ray imaging sub-system and will be described with particular respect thereto.

Atherosclerotic cardiovascular disease, especially some aspects of coronary heart disease (CHD), has been thought to develop gradually. In recent years, it has become known that occlusion may occur suddenly, potentially resulting in thrombus formation and angina, myocardial infarction (MI) or sudden death. This shift in study of one operative mechanism for CHD is related to evolving understanding of different types of plaque in coronary arteries that may cause acute coronary syndromes. Present study of plaque in CHD involves identification, characterization and location of plaque including, more specifically, the roles of stabilized plaque and vulnerable plaque in CHD.

Stable plaque is characterized as having a fibrous rich cap over a liquid core. A vulnerable plaque, which may be more likely to erode or suddenly and unpredictably rupture, is less fibrous, has less muscularity, more lipids and inflammatory cells. Particularly vulnerable plaque is characterized as having a thin fibrous coating over a large, lipid rich core that contains numerous inflammatory cells. Vulnerable plaque includes various high-risk plaques thereby predisposing patients to develop acute thrombotic coronary syndrome.

The atherosclerotic plaques are not merely an accumulation of cholesterol on the artery wall. They include an active collection of different migrated, proliferated and infiltrated cells such as mainly smooth muscle cells and immune cells along with one or more immune-triggering agents such as oxidized LDL, infectious agents, heat shock proteins as well as other factors. These metabolically active vulnerable plaques can remain quiescent and sub-clinical for years then erode or suddenly erupt with an associated deleterious effect on the cardiac system.

Failure of present methods to identify future acute coronary syndromes has led to a search for more effective diagnostic techniques. One example of a present diagnostic technique that is not as successful as desired is the failure of coronary angiography to predict catastrophic cardiovascular failure. One reason for this is vulnerable plaques are usually angiographically non-significant.

Some techniques that are under study to identify, locate and characterize plaque in the coronary arteries include invasive and non-invasive methods. At present, the clinically available techniques tend to have disadvantages that limit their use in asymptomatic patients or are not as effective as desired in identifying, locating and characterizing vulnerable plaque which are believed to represent the higher risk of fatal CHD.

Some examples of invasive techniques presently under evaluation include angiography, Intravascular Ultrasound, Intravascular Thermography, Optical Coherence Tomography, Intravascular Electrical Impedance Imaging, Photonic Spectroscopy, as well as a number of other Spectroscopy techniques. Conventional non-invasive techniques being studied for plaque identification, location and characterization include MRI (including contrast media), Electron Beam CT, multi-slice and spiral CT as well as conventional Nuclear imaging.

Even with such diverse diagnostic techniques under development and study for the early identification of vulnerable plaque, the degree of clinical effectiveness is presently less than desired in a clinically practical setting. One reason is that some of these imaging modalities primarily provide anatomical information and, given the composition and metabolic activity associated with vulnerable plaque, functional information is particularly useful in determining whether a plaque deposit is stable or vulnerable. However, eventhough conventional nuclear medicine imaging techniques can provide functional images, the total volume of vulnerable plaque is extremely small and the total plaque uptake of tracers used in nuclear medical imaging is somewhat limited. Consequently, the application of conventional nuclear medicine clinical techniques using SPECT and PET for plaque detection has not yet provided a clinically acceptable technique that generates clinically practical diagnostic results. More specifically, when considering typical plaque deposits and tracer uptake amounts, the small volume of the plaque deposits and limited uptake of tracers result in low count acquisition rates. In order to obtain clinically useful images with such low count acquisition rates, scanning time would need to be increased perhaps 40 fold over that of a typical myocardial perfusion scan. This scale of increase in scanning time is not clinically practical.

In addition, other risks associated with the invasive techniques may make them less desirable for office based clinical application, particularly for the asymptomatc patient population. Diagnostic imaging systems such as MRI or CT may be cost prohibitive in an office based practice. Present clinical techniques for conventional full application nuclear medicine systems (SPECT and PET) have clinically unacceptable scanning time resulting from count rate limitations as discussed above. Furthermore, many available full feature tomographic nuclear medicine systems may have cost and space considerations making them less desirable for office based clinical screening of patients.

It is desirable to have an apparatus and method for a less expensive, compact, non-invasive, clinically practical diagnostic imaging technique that provides anatomical and functional information to identify, locate and characterize vulnerable plaque for widely used preliminary screening and early detection of CHD in the general population. It is also desirable to have a system that provides high resolution, relatively large field of view and good clinical sensitivity in an office based clinical setting.

SUMMARY OF THE INVENTION

The present invention is directed to a diagnostic imaging system that satisfies at least some of the needs recited above to provide a diagnostic imaging system for plaque detection, location and characterization which is clinically practical. An apparatus in accordance with one embodiment illustrating a diagnostic imaging system having aspects of the present invention comprises a computer workstation for controlling the imaging system, interfacing with an operator and generating images. A coordinate system is in data communication with the computer workstation and is adapted to describe relative position of imaging system components within the diagnostic imaging system. A subject support is included which is describable within the coordinate system. An X-ray sub-system is positionable around the subject support. Position sensors are operatively connected to the x-ray sub-system, the position sensors providing signals to the workstation indicative of the position of components of the x-ray sub-system within the coordinate system. A nuclear camera sub-system is also positionable around the subject support and associated position sensors are operatively connected to the nuclear camera sub-system. The position sensors providing signals to the workstation indicative of position of components of the nuclear camera sub-system within the coordinate system. The nuclear camera sub-system includes a planar gamma camera and a pinhole collimator. The workstation includes a region of Interest position determination function for determining the position within the imaging system of a region of interest in an image generated by the x-ray sub-system. The region of interest to be precisely targeted for imaging by the nuclear camera.

The coordinate system that describes relative position in the imaging system may be a two dimensional system in a selected plane or a three dimensional system describing relative positions within a volume associated with the imaging system.

The diagnostic imaging system may include a region of interest comparison database having a reference image and means for determining a region of interest in an image generated by one sub-system of the imaging system by comparing the generated image and the reference image of the comparison database.

A method in accordance with principles of the present invention includes positioning a first imaging modality for imaging a subject and generating image data of the subject from the first imaging modality. The method includes evaluating the image data from the first imaging modality and identifying a region of interest in the imaged subject from the evaluated data. Next, the method includes the step of determining the position for the region of interest in a coordinate system from the first image data and positioning a second imaging modality at the region of interest using the determined position of the region of interest.

The method may include, in the step of identifying a region of interest in the imaged subject, the step of comparing the image data from the first modality to a reference image stored in a database.

The precise targeting of the nuclear camera using the images from the x-ray system to obtain a precise image of the region of interest significantly improves the image toward an optimized imaging alignment as well as improving the imaging protocol toward an optimized protocol.

An apparatus and method applying principles of the present invention provides the foregoing and other features hereinafter described and particularly pointed out in the claims. The following description and accompanying drawings set forth certain illustrative embodiments applying principles of the present invention. It is to be appreciated that different embodiments applying various principles of the invention may take form in various components and arrangements of components. These described embodiments being indicative of but a few of the various ways in which the principles of the invention may be employed independently or combined in various combinations without limiting the breadth of scope of the claims. The drawings are only for the purpose of illustrating an embodiment in accordance with the patent requirements of an apparatus applying principles of the present invention and are not to be construed as limiting the invention to the particular illustrated structure.

BRIEF DESCRIPTION OF THE DRAWINGS

The foregoing and other features and advantages of the present invention will become apparent to those skilled in the art to which the present invention relates upon consideration of the following detailed description of embodiments illustrating aspects and features of the invention with reference to the accompanying drawings, wherein.

DETAILED DESCRIPTION

Figure 1:
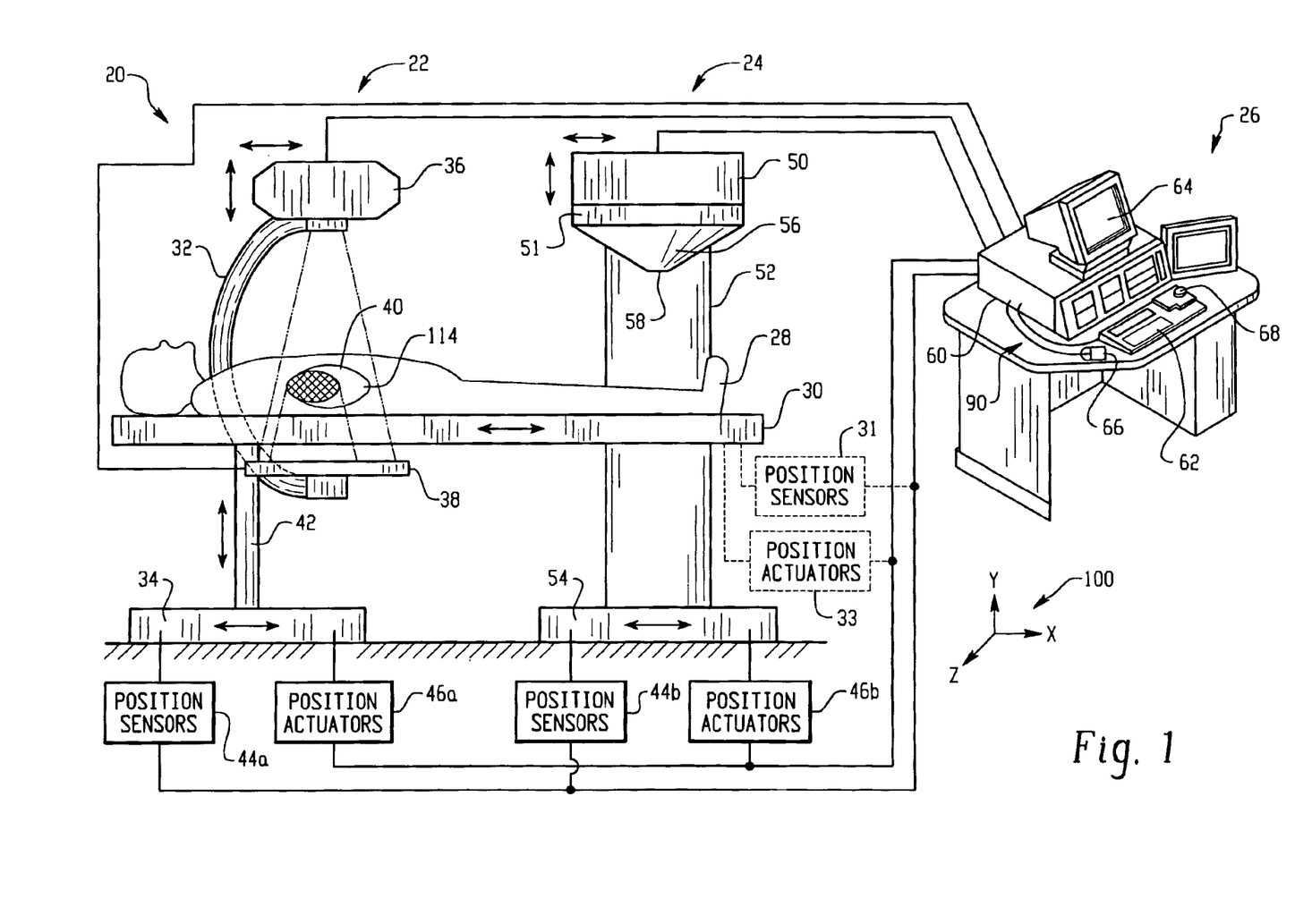
FIG. 1 is a schematic representation of an imaging system illustrating features according to principles of the present invention.

With reference to FIG. 1, a diagnostic imaging system 20 includes an X-ray sub-system 22, a nuclear camera sub-system 24 and a control console 26. An imaging subject 28 is supported on a subject support 30 in an examination region of the diagnostic imaging system 20.

The X-ray diagnostic imaging sub-system 22, such as a fluoroscopic and/or radiographic imaging system, includes a support member 32 that is attached to a moveable floor mounted base structure 34. The support member 32 may be coupled to the base structure 34 with a telescopic support column member 42. In the embodiment being described, the support member 32 includes a C-arm.

An x-ray source or tube 36 is secured to a first free end of the support member 32, and an opposing x-ray detector 38 is secured to a second free end of the support member 32. A fluoroscopic/radiographic examination region is defined between the x-ray source 36 and x-ray detector 38. The x-ray source 36 and x-ray detector 38 can be positioned relative to the imaging subject 28 and subject support 30 such that the positions of the components of the x-ray sub-system 22, subject support 30 and subject 28 are known or determinable through geometric relationships such that a Region Of Interest (ROI) 40 in the imaging subject 28 can be sufficiently located within a coordinate system 100 (FIG. 2) for the diagnostic imaging system 20. The coordinate system 100 is schematically represented in the real space of the imaging system 20 by the X, Y, Z axes in FIG. 1. Alternatively, a suitable two dimensional coordinate system may be used.

The x-ray tube 36 includes a housing that supports a fixed or rotating anode x-ray tube with an integral or separate high-voltage power supply. The x-ray detector 38 includes a housing which supports, for example, a flat panel image receptor, as is known in the art. The flat panel image receptor may include solid state detector crystals or a planar substrate such as glass laminated with an array of sensors such as amorphous silicon crystals that convert x-ray energy to electrical signals. That is, the solid state detector crystals or sensors emit an electric potential when struck by photons of x-ray energy. The magnitude of the potential is related to the intensity of the x-ray beam. The electrical signals can be read out from a row/column matrix and then converted to digital data. The data can then be processed in the control console 26 to be used in accordance with other features and principles of the present invention and to display suitable images.

The amorphous silicon flat panel image receptor is compact in size and weight and replaces a conventional image intensifier tube, thus reducing the size of the x-ray detector 38. Further, the flat panel image receptor provides a rectangular image, eliminates the distortion of an image common to conventional image intensifier tubes, and provides constant image quality across the flat panel of the image receptor, thus minimizing the amount of panning typically required with conventional image intensifier tubes. It should be appreciated that the flat panel image receptor can be of any suitable dimension, and the system can be easily upgraded to incorporate larger flat panel image receptors. It is to be understood that, eventhough a flat panel detector is described as having various advantages in this embodiment, conventional image intensifier tubes may also be used in accordance with aspects according to the principles of the present invention.

Position sensors 44a are operably located throughout the x-ray sub-system 22 and are suitably in communication with the control console 26 such that the location of the x-ray sub-system components can be accurately determined within the coordinate system 100. Position actuators 46a are operably connected to the control console 26 to controllably move components of the x-ray sub-system 22 and to position the components of the sub-system as directed by an operator or by automated instructions received from the control console 26. Various known modes of positioning moveable components are contemplated for the actuators such as motors, manual or solenoid-driven interlocks and/or position switches can be utilized to control or limit the movement of the various components of the x-ray diagnostic sub-system including the base member 34, x-ray support 32, source 36, detector 38 and the column member 42. It is contemplated that the position sensors 44a can verify or confirm the position of the x-ray sub system components to suitably locate the Region Of Interest 40 of the subject 28 in the coordinate system 100 of the diagnostic imaging system 20.

When activated at the control console 26, the diagnostic imaging system 20, and, in particular, the exposure of the x-ray source 36, can be either continuous or pulsed. In the pulsed mode, radiography procedures can be performed, such as CINE, Spot Film and DSA, thereby generating radiographic image representations. The x-ray source 36 can be gated on and off in the pulsed mode using a conventional grid control circuitry or a pulse fluoro high-voltage power supply.

The nuclear camera sub-system 24 may be a planar nuclear gamma ray detector or a Single Photon Emission Computed Tomography (SPECT) system. The nuclear detector includes a camera head 50 which receives radiation emanating from the subject 28 and produces output signals indicative thereof. As is conventional in the art, the camera head 50 includes a detector assembly 51 which may be comprised of solid state detector crystals of cadmium zinc telluride (CZT) or other suitable solid state devices to directly provide signals useful for generating diagnostic images. Alternatively, the detector assembly 51 may include a scintillation crystal which provides light flashes or scintillations in response to incident radiation. For a detector assembly utilizing the scintillation crystal, an array of photomultiplier tubes detects each scintillation event. The solid state detector or photomultiplier tubes are connected with position determining circuitry to ascertain the location of each received radiation event or scintillation, its energy, and other characteristics and produce the output signal which is indicative thereof.

The crystal area within the detector assembly 51 may be a planar crystal assembly and have dimensions of 40 cm by 40 cm. The crystal has an intrinsic resolution of 4.0 mm at 140 keV. A pinhole collimator 56, is attached to the camera head 50. The pinhole collimator 56 has an aperture 58, comprised of lead, that is approximately 2.0 mm in diameter and the acceptance angle of the pinhole collimator is 53°. The distance from the aperture 58 to the surface of the crystal of the detector assembly 51 is 40.0 cm. Using these specifications for the pinhole collimator 56 and camera head 50 to image a plane located 10 cm (a suitable depth for cardiac imaging) within the subject 28, the magnification factor is 4. The field-of-view is about 10.0 cm in diameter and the resolution is 2.7 mm. The cardiac region has a diameter of about 7 cm and plaque is usually found in the first few centimeters of the coronary arteries. Thus, as further described below, accurate and precise targeting of the pinhole collimator and camera head assembly over this Region Of Interest 40 requires only a single imaging event for the location, identification and characterization of plaque in the cardiac arteries. This precise targeting improves imaging acquisition and imaging protocol.

Image processing and reconstruction circuitry in the control console 26 processes the output signals of the camera head 50 as it provides signals during an examination into an image representation. The image representation may be displayed on a video monitor, stored in computer memory, stored on tape or disk for later recall, further processed, or the like.

A camera head support 52 supports the camera head 50. The support 52 may be adapted to include telescopic components and other coupling members that can position the camera head 50 along a desired axis definable in the coordinate system and can move it within the space described by the coordinate system 100. A camera base structure 54 may be controllably moveable along the floor and supports the gantry 52.

Position sensors 44b are operably located throughout the nuclear camera sub-system 24 and are suitably in communication with the control console 26 such that the location of the system components can be accurately determined within the coordinate system 100. Position actuators 46b are operably connected to controllably move components of the nuclear camera sub-system 24 and to position the components of the sub-system as directed by an operator or by automatic instructions received from the control console 26. Various known modes of positioning moveable components are contemplated for the actuators such as motors, manual or solenoid-driven interlocks and/or position switches can be utilized to control or limit the movement of the various components of the nuclear camera including the base member 54, support 52, camera head 50, collimator aperture 58, and the column member support 52. It is contemplated that the position sensors 44b can verify or confirm that the nuclear camera sub-system components have been properly placed to target and suitably image the Region Of Interest 40 of the subject 28 in the coordinate system 100 of the diagnostic imaging system 20.

The imaging system control console 26 coordinates the operation of the sub-systems 22, 24. All of the control and imaging processing functions in the illustrated components and systems can be performed by known computer based systems having an operable complement of component systems such as suitable processors 60, memory and storage, input, output and data communications capabilities.

An operator interface 90 includes input and output devices suitably in communication with the control console 26 such as a keyboard 62, a touch screen monitor 64, a mouse 66, a joystick (not shown), a track ball 68 as well as other input apparatus or devices to provide operator instructions to control the imaging system and locate the region of interest 40 in an image displayed on the monitor 64.

Figure 2:
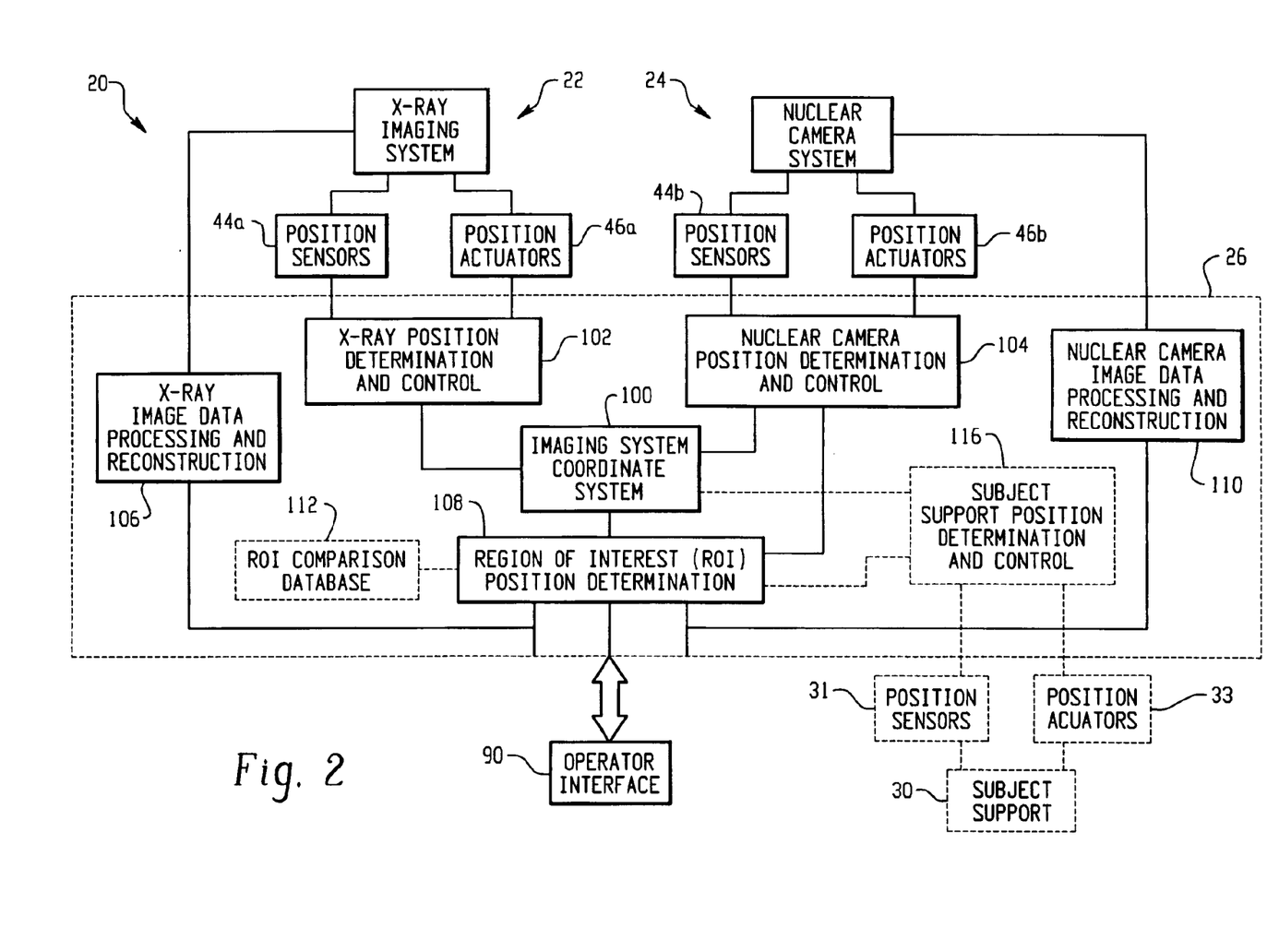
FIG. 2 is a block diagram representation of an imaging system illustrating aspects of a diagnostic imaging system according to principles of the present invention.

Turning now to FIG. 2, a block diagram of the diagnostic imaging system 20 is shown illustrating in more detail functions performed within the control console 26 in accordance with principles of the present invention. The X-ray sub-system 22 is connected to its associated position sensors 44a and actuators 46a which are operatively connected to an x-ray position determination and control function 102. The x-ray position determination and control 102 receives position sensor information and is in data communication with the imaging system coordinate system 100. The combination of position sensor information with the coordinate system is used to locate components of the x-ray sub-system 22 within the coordinate system 100 and relative to other components of the diagnostic imaging system 20 and subject 28. The control 102 is controllably connected to, and provides control signals to, the actuators 46a to position the components of the x-ray sub-system 22.

The nuclear camera sub-system 24 is connected to its associated position sensors 44b and actuators 46b which are operatively connected to a nuclear camera position determination and control function 104. The nuclear camera position determination and control 104 receives position sensor information and is in data communication with the imaging system coordinate system 100. The combination of position sensor information with the coordinate system 100 is used to locate components of the nuclear camera sub-system 24 within the coordinate system 100 and relative to other components of the diagnostic imaging system 20 and subject 28. The control 104 is controllably connected to, and provides control signals to, the actuators 46b to position the components of the nuclear camera sub-system 24.

The coordinate system 100 provides a framework to describe the positional relationship between the components of the imaging system 20 in response to position sensor signals, known geometric relationships between components and the subject 28, as well as operator input through the control console input devices. For example, the operator may use a touch screen monitor 64 to highlight a selected ROI 40 of the subject 28 on an x-ray image displayed on the monitor 64. Once the ROI 40 is identified by the operator, the coordinate system provides the actual coordinates of the ROI in the subject 28 within the examination space represented and defined by the coordinate system. The position of ROI identified and marked by the operator on the x-ray image is provided so that the nuclear camera head 50 can have the pinhole aperture 58 accurately positioned at the ROI 40 either manually or by the nuclear camera position determination and control 104 and actuators 46b. In effect, the coordinate system 100 is used in determining the targeting coordinates in the real space of the imaging system 20 that are used to provide control signals to the position actuators 46b or assist the operator to manually locate the aperture 58 of the pinhole collimator 56 at the actual Region Of Interest 40 to be imaged in the subject 28.

The coordinate system 100 may be a three dimensional system capable of defining the positional relationship of imaging system components within the defined volumetric space or an advantageously oriented planar two dimensional coordinate system such that the control console 26 or operator may monitor and control the movement of the components. Either coordinate system may be manually or automatically coordinated or registered by the operator using images on the monitor 64 and may include markers or fiducals that are visible on the monitor and in the images. The orientation of a planar coordinate system may be advantageously selected to provide a desired reference system that is beneficial for imaging the particular subject or ROI while in a specific orientation during the imaging process. The coordinate plane may be advantageously adapted for different imaging planes and subject orientations.

Figure 3:
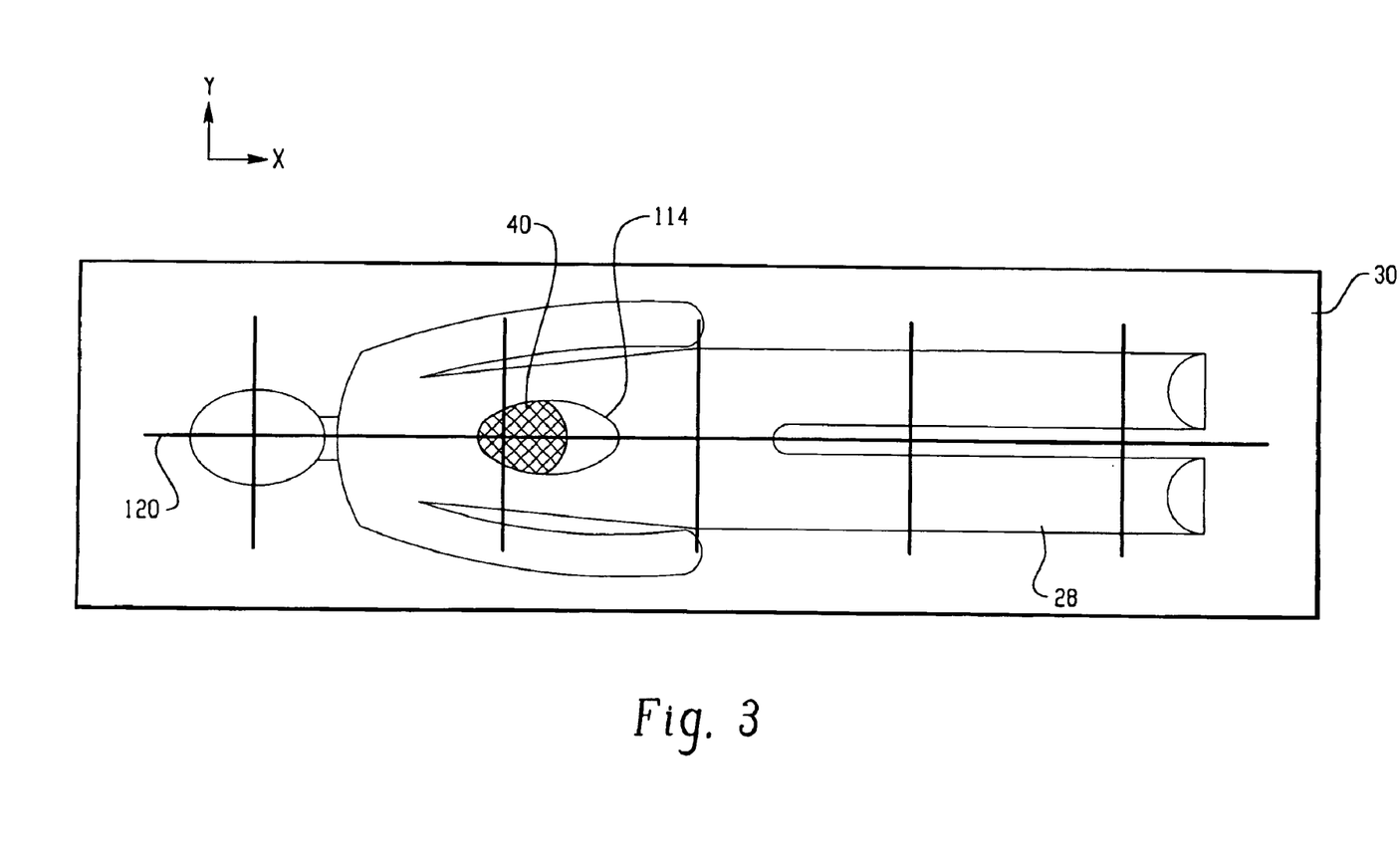
FIG. 3 is a schematic representation of a patient support applicable with principles of the present invention.

Referring briefly to FIG. 3, an example is illustrated of a subject support 30 that is adapted for one possible implementation of a two dimensional planar coordinate system for use with an embodiment applying aspects of the present invention. The subject 28 is imaged on a support 30 having a reference marker 120 embedded within the support 30. The reference marker 120 is comprised of known material that is detectable by at least one of the sub-systems 22, 24 in the resulting image data or images. The reference marker 120 may take any of a number of configurations such that a sufficient number of reference marks are provided to accurately locate the ROI 40 within the system coordinate system 100 relative to components of the imaging system 20. It is contemplated that known geometric relationships between system components and position sensor input may be used with this example. This accurate location of the ROI 40 results in providing information for the desired targeted placement of the nuclear camera 50 to successfully image the ROI 40 in accordance with the principles of the present invention. The reference marker 120 may be a set of axes at advantageous angles and/or intervals, a Cartesian grid structure or other suitable combination of relational marks that can be used to specifically locate the ROI in the coordinate system 100.

Returning to FIG. 2, The x-ray imaging sub-system 22 provides image data, generated by operating the x-ray sub-system 22 on the subject 28 in the examination region, to an x-ray image data processing and reconstruction function 106 which provides all necessary image processing, communication and storage functions to generate an image suitable for display in human readable form. For example, an image of a portion of the subject may be viewable on a monitor 64 of the operator interface 90. The processing and reconstruction function 106 also provides processed information to be used in accordance with other functional aspects of the present invention. The x-ray image data processing and reconstruction function 106 is operatively connected to the operator interface 90 and a Region of Interest (ROI) position determination function 108.

The ROI position determination function 108 is also operatively connected to the coordinate system 100 and the operator interface 90. The ROI determination function 108 uses the coordinate system 100 and position information about the imaging system 20 components, image information from the x-ray sub-system 22, and ROI 40 identification input provided by the operator or an automated ROI identification and position (as described below with respect to a comparison to a database) to determine the proper coordinates of the ROI 40 in real space to properly position the nuclear camera 50 to target and obtain an image of the ROI 40 in the subject 28 with the nuclear camera system 24. The ROI position determination function 108 is further connected to the nuclear camera position determination and control 104 in the event that the determined coordinates for the ROI 40 are provided to the control 104 for the generation of commands for automatic positioning of the nuclear camera system 24 using the actuators 46b.

The nuclear camera sub-system 24 provides image data, generated by receiving emission data from the detector in response to radiation received from the subject 28 in the examination region, to a nuclear camera data processing and reconstruction function 110 which provides all necessary image processing, communication and storage functions to generate an image suitable for display in human readable form, for example, on a monitor 64 of the operator interface 90. The nuclear camera image data processing and reconstruction function 110 is operatively connected to the operator interface 90 and the Region of Interest (ROI) position determination function 108. The processing and reconstruction function 110 also provides processed information to be used in accordance with other functional aspects of the present invention. For example, data may be in a format that facilitates verification of coordinates of the area imaged by the nuclear camera such that the nuclear image of the ROI 40 may be compared to the coordinates of the ROI 40 as determined earlier in the ROI determination function 108.

In another embodiment of functions that may be included in the control console 26, a ROI comparison database 112 is in data communication with the ROI position determination function 108. The database 112 stores representative images of particular organs to be imaged with the sub-systems 22, 24, for example, a heart 114. Associated with the stored image of the heart is the relative position of the particular portion of the heart which is a desired Region of Interest in the subject 28. For example, the stored heart image data includes the relative location information for the area of the coronary arteries (an area approximately 5 cm×10 cm) relative to the remainder of the heart image. The coronary arteries are targeted in this example since it is one area where vulnerable plaque can initially appear indicating CHD. The recalled stored image and corresponding region of interest from the comparison database 112 may be registered with the actual x-ray image of the subject in the ROI Determination function 108. The registration may be done automatically or manually using known rigid registration or non-rigid registration techniques. Once the actual image and reference image are registered, the coordinates of the ROI as defined in the reference image are combined with the actual image to determine the position of the ROI 40 for the subject to be examined in the diagnostic imaging system 20. As such, specifically targeting a portion (the ROI) of the heart for use with the pinhole collimator requires (i) locating the heart within the subject and within the coordinate system and (ii) similarly locating and identifying the smaller portion of the heart to be imaged within the coordinate system using operator input or the comparison database 112. Depending on a particular diagnostic procedure, organs other than the heart or features of the subject and specific target areas are contemplated for selection as a Region of Interest.

In operation of the described apparatus, a method is disclosed illustrating principles of the present invention using the diagnostic system having combined nuclear medicine and x-ray imaging sub-systems. As discussed above the primary difficulty for plaque detection using conventional SPECT imaging is poor count acquisition statistics to locate and characterize plaque. For example, a conventional scan protocol with a pixel size of 0.64 cm and having the following parameters (i) Myocardial perfusion uptake ~1 $\mu$Ci/ml, (ii) Plaque uptake ~0.25 $\mu$Ci/ml, (iii) plaque dimensions 0.2 mm thick, length 5.0 mm and circumference 20 mm and (iv) plaque uptake to background ratio (PBR) 100:1 in volume space. Under these conditions the total plaque uptake per voxel is about 40 times less than for a conventional cardiac perfusion scan using Thallous Chloride $^{201}$Tl. As mentioned above, this results in scan data acquisition times that are not acceptable for a clinically practical application.

In a number of instances the projected plaque thickness will be greater than one bin due to the magnification factor associated with using the described pinhole collimator with the nuclear camera. As such, the required counts are lower. It has been determined that the feasibility of suitable plaque detection is influenced by (i) plaque to background ratio and (ii) sensitivity of the nuclear camera with the parameters of pinhole collimator. For a suitable example additional parameters of the imaging system to apply principles of the present invention, in addition to the conventional scan parameters recited above, include (i) the Thorax volume size is ~400 mm, (ii) bin size, pixel size of the planar image and voxel size of the subject volume is ~2.5 mm and (iii) the distance from the pinhole aperture to the ROI ~100 mm. For the instance where plaque covers the entire inner surface of a blood vessel, the thickness of the plaque projection on the planar image can be as high as 12 bins and the plaque to background ratio can be as high as 1.15. In a more conservative determination of plaque coverage within a vessel, when a plaque to background ratio of 1.10 is used and the plaque projection thickness is 4 bins, the counts per pixel for the plaque to be visible can be as low as 4–8 CPP. An accurately targeted pinhole nuclear camera system can provide statistically significant images under this plaque to background ratio at 4 counts per pixel with a system resolution of 2.7 mm in a clinically acceptable time of approximately 48 minutes. By increasing the aperture size from 2.0 mm to 2.4 mm, the system resolution is degraded to 3.0 mm and a clinically useful diagnostic image having 4 counts per pixels can be obtained within approximately 33 minutes. An additional reduction in scan time is obtainable by collapsing the planar image matrix from 128 squares to 64 squares. This results in a decrease in acquisition time by a factor of approximately 4 to about 10 minutes for a planar image suitable for plaque detection. However, collapsing the image matrix results in a degradation of resolution to about 5 mm.

Turning now to a description of a method in accordance with principles of the present invention and applying the parameters recited above, a subject 28 is placed on the support 30 in the examination region of the x-ray sub-system 22 and the position sensors 44a and 44b provide the relevant component position information signals to the x-ray position determination and control 102 and nuclear camera position determination and control 104. The relevant position coordinates of components of the x-ray sub-system 22 and nuclear camera sub-system 24 are determined with this position information and data from the coordinate system 100. The component position coordinates for the x-ray sub-system 22 are then provided to the ROI position determination function 108. The operator actuates the x-ray sub-system 22 to generate image data from the detector 38. The image data is provided to the x-ray image data processing and reconstruction function 106. The image data is processed in a known manner and an image is provided to the monitor 64 of the operator interface and suitable data is also provided to the ROI position determination function 108. The x-ray sub-system provides anatomical image data to identify the anatomical region of interest that corresponds to the functional image region of interest. More specifically, in this example, the x-ray localizes the cardiac ROI to be planar imaged with the nuclear gamma camera 50.

In one implementation of the imaging system applying methods in accordance with the principles of the present invention, the operator views the x-ray image on the monitor 64. The ROI position determination function 108 correlates the coordinates of the image visible on the monitor with the imaging system coordinate system 100. Viewing the image, the operator may use any of the input devices or means to selectively and specifically identify and target the visible ROI 40 and thereby enter that specific position. Alternatively, the control console 26 may automatically determine the ROI 40 using the ROI comparison database 112 as described above. Once the ROI is determined, the ROI position determination function 108 provides the targeted ROI 40 coordinates in response to the operator identified position from the image to the nuclear camera position detection and control 104. The nuclear camera position determination and control 108 provides control signals to the actuators 46b to accurately position the aperture 58 of the pinhole collimator 56 over the identified ROI 40.

Alternatively, the nuclear camera detector head 50 may be positioned manually and the position sensors 44b may provide position information to the position determination and control function 104 which, in turn, provides the camera head 50 position information to the ROI position determination and operator interface. The position of the camera head 50 and aperture 58 may be visibly represented on the monitor such that the operator may visually confirm when the nuclear imaging system is positioned at the ROI 40 to obtain the planar nuclear image.

At the appropriate time, a radiopharmaceutical is introduced into the subject 28 such that the nuclear medicine image may be acquired. Using the apparatus and method of the present invention, conventional radiophamceuticals for cardiac applications may be used due to the advantageous resolution and sensitivity in accord with the described parameters for the nuclear camera and pinhole collimator in combination with the precise targeting of the nuclear camera provided by using the anatomical image and coordinate system to locate the ROI.

It is also contemplated that radiopharmeceuticals that have increased binding specificity to plaque deposits, particularly vulnerable plaque, relative to adjacent normal tissue may be used in accordance with the principles of the present invention. A suitable class of reagent is more fully described in U.S. Pat. No. 6,375,925 entitled Method and Reagents for Non-Invasive Imaging of Atherosclerotic Plaque, issued to Tsimikas et al., which is fully incorporated herein by reference.

In another embodiment of a system applying principles in accordance with the present invention, the subject support 30 serves as the subject positioning assembly and support structure. The support 30 may also be movably controlled by the imaging system control console 26 to coordinate movement of the subject 28, with respect to operation of the imaging sub-systems 22 and 24, to obtain subject imaging information at one or more desired locations along the length of the subject 28. The support 30 is capable of longitudinally extending the subject through the respective examination regions of the imaging sub-systems 22 and 24, as may be desired or suitable for image data acquisition. In this implementation, the support 30 is moved to position the subject in the examination region of the x-ray sub-system 22 to acquire the anatomical image to be used in determining ROI 40. Once the x-ray image is obtained, the ROI is determined as described above. The subject is then positioned under the nuclear camera 50 by moving the support 30. The support 30 has suitable position sensors 31 and position actuators 33 and the control console may include an appropriate subject support positioning and control function 116 suitably connected to the other control console functions to implement the positioning features of the present invention.

Figure 4:
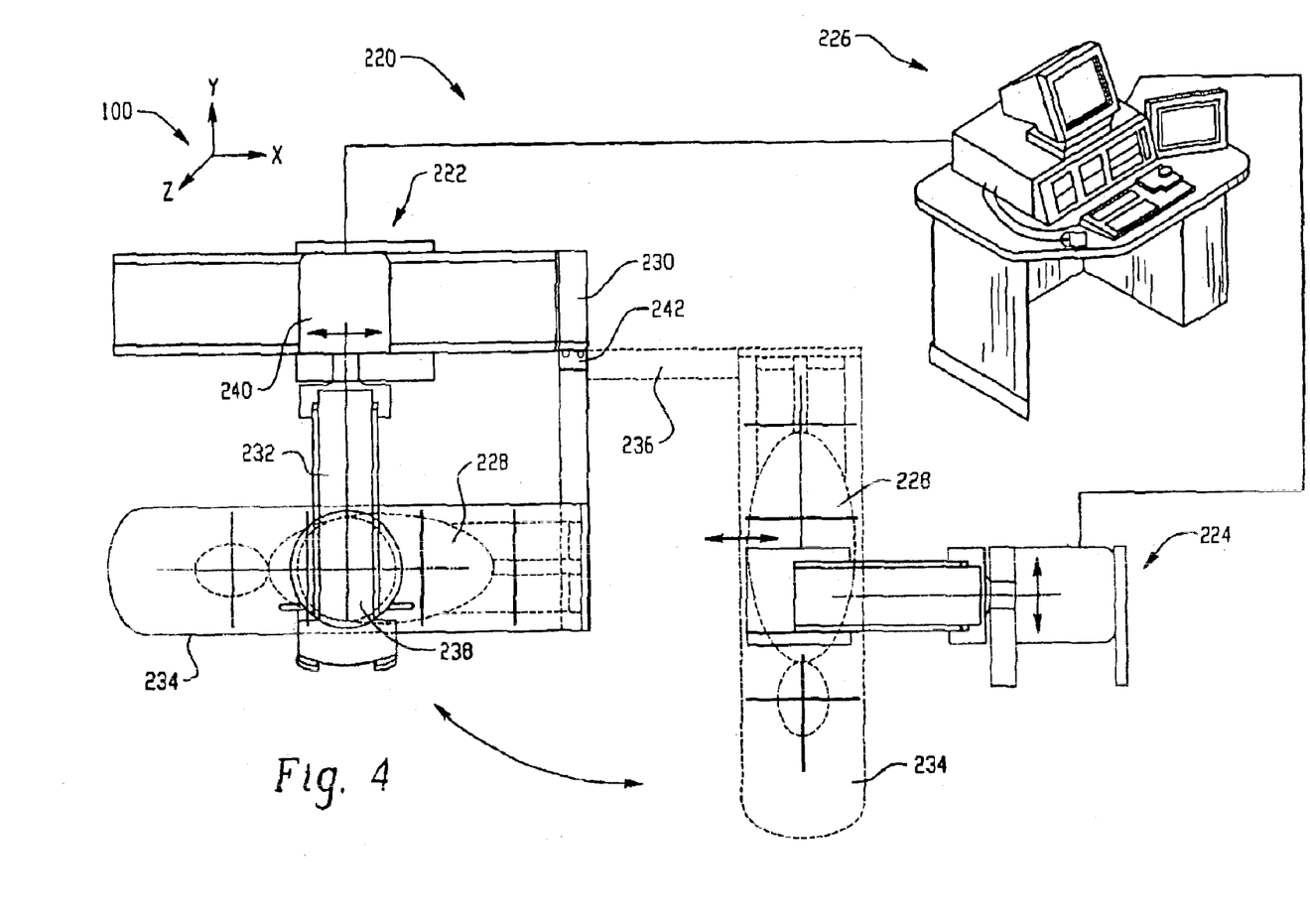
FIG. 4 is a schematic representation of another embodiment of a diagnostic imaging system in accordance with principles of the present invention.

Referring to FIG. 4, another embodiment of a diagnostic imaging system 220 is shown which includes aspects in accordance with principles of the present invention. The system includes an x-ray sub-system 222, a nuclear sub-system 224 and control console 226, all having the functionality as described above for corresponding elements in the previously described embodiments. This embodiment of an apparatus consists of a stand 230, an x-ray sub-system component support 232, and a subject support 234 which is connected to the stand, via a supporting arm 236, and serves to carry the subject to be imaged. The component support 232 is in this case formed by a C-arm and the imaging components are formed by an X-ray source 238 and an X-ray detector (not shown in this view) which are mounted on the C-arm. The C-arm is attached to a carriage 240 which is displaceable in the longitudinal direction (as denoted by the arrow on the carriage). The X-ray tube and the X-ray image detector can be adjusted in such a manner that the subject 228 to be imaged can be irradiated in desired directions and from desired positions to satisfy the principles of the invention for locating and targeting a particular ROI.

The supporting arm 236 is rotatable about a pivot 242 connected to the stand 230. The subject support 234 is also shown in the swung away position, as shown in dashed lines. Locking means (not shown in the Figure) may be provided for locking the position of the support 234 swung away around the pivot 242, so that it remains locked in the swung away position at a location known within the coordinate system for targeting the ROI during nuclear imaging of the subject. The location of the support 234 in both sub system positions is known in the coordinate system 100 and precise targeting of the ROI for the nuclear image is performed in a manner similar to that described above.

Figure 5A:
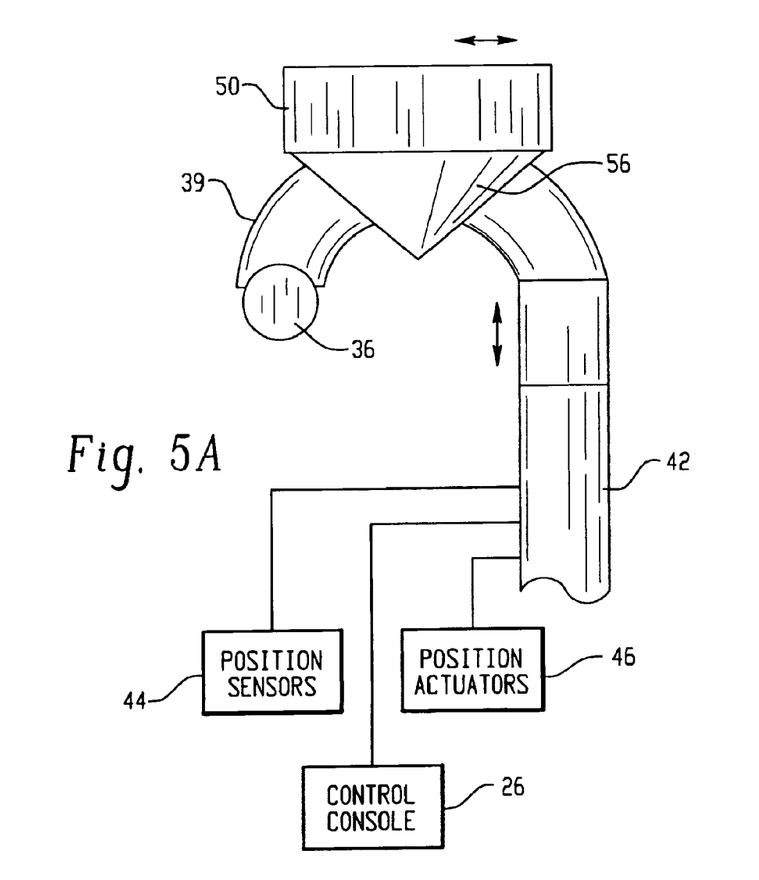
FIGS. 5A & 5B are schematic representations of an alternate embodiment of an apparatus applying principles of the present invention.
Figure 5B:
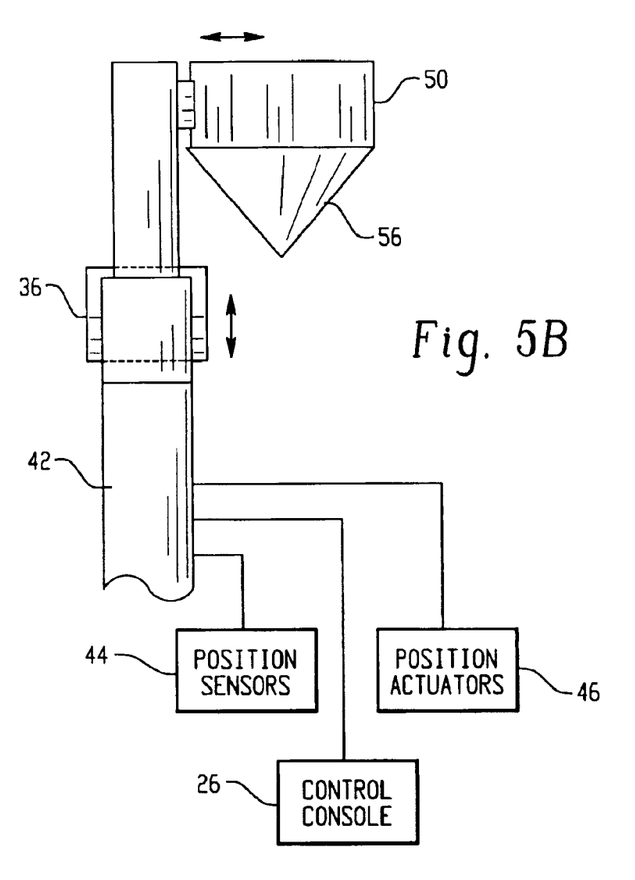

Referring to FIGS. 5A and 5B, another embodiment of an apparatus applicable with principles of the present invention is shown. Common elements, or elements having similar functionality with previously described elements, are shown with similar reference numerals. The x-ray tube 36 is secured to a positionable support member 39. The camera head 50 is also attached to the same support member 39. The support member 39 is attached to the telescopic support member 42 that is subsequently coupled to a moveable base (not shown). Position sensors 44 are operably connected to suitable portions of the various support structures to provide signals indicative of the positions of the x-ray source 36 and camera head 50 to the control console 26. Position actuators 46 are controllably connected to the control console to position the x-ray source 36 and nuclear camera detector 50, as indicated by the arrows, to suitably identify the region of interest 40 with the x-ray system as well as precisely target the nuclear camera head to obtain the desired image of the region of interest according to principles of the present invention. In effect, the embodiment in FIGS. 5A and 5B include a common support structure, controlled by the control console, for both of the x-ray source and nuclear camera.

While a particular feature of the invention may have been described above with respect to only one of the illustrated embodiments, such features may be combined with one or more other features of other embodiments, as may be desired and advantageous for any given particular application. From the above description of the invention, those skilled in the art will perceive improvements, changes and modification. Such improvements, changes and modification within the skill of the art are intended to be covered by the appended claims.

What is claimed is:

1. A diagnostic imaging system, the system comprising:
   a computer workstation for controlling the imaging system, interfacing with an operator and generating images;
   a coordinate system in data communication with the computer workstation, the coordinate system adapted to describe relative position in the diagnostic imaging system;
   a subject support describable within the coordinate system;
   an x-ray sub-system, the x-ray sub-system positionable around the subject support;
   position sensors operatively connected to the x-ray sub-system and workstation, the position sensors providing signals to the workstation indicative of the position of components of the x-ray sub-system within the coordinate system;
   a nuclear camera sub-system, the nuclear camera sub-system positionable around the subject support;
   position sensors operatively connected to the nuclear camera sub-system and workstation, the position sensors providing signals to the workstation indicative of the position of components of the nuclear camera sub-system within the coordinate system;
   means for determining the position within the imaging coordinate system of a region of interest in an associated imaging subject from an image generated by the x-ray sub-system; and
   means for targeting the nuclear camera sub-system to precisely obtain an image at the region of interest.

2. The diagnostic imaging system of claim 1 wherein the coordinate system is a two dimensional system describing the relative position of components in the imaging system in a selected plane.

3. The diagnostic imaging system of claim 1 wherein the coordinate system is a three dimensional system describing the relative position of components within a volume associated with the imaging system.

4. The diagnostic imaging system of claim 1 wherein the x-ray sub system includes and x-ray source and x-ray detector and the nuclear camera sub-system includes a nuclear camera detector head, the diagnostic imaging system including a gantry, the gantry providing a positioning support structure, the support structure commonly supporting and positioning both of the x-ray source and nuclear camera detector head.

5. The diagnostic imaging system of claim 1 including:
   a region of interest comparison database having a reference image; and means for determining a region of interest in an image generated by one sub-system of the imaging system by comparing the generated image and the reference image of the comparison database.

6. The diagnostic imaging system of claim 1 wherein the nuclear camera sub-system includes:
   a planar gamma camera head; and
   a pinhole collimator.

7. The diagnostic imaging system of claim 6 wherein the pinhole collimator is a multiple hole pinhole collimator.

8. The diagnostic imaging system of claim 1 including means for positioning components of the x-ray sub system and nuclear camera sub-system, the means for positioning controllably connected to the workstation.

9. A diagnostic imaging system, the system comprising:
   a computer workstation for controlling the imaging system, interfacing with an operator and generating images;
   a coordinate system in data communication with the computer workstation, the coordinate system adapted to describe relative position of components in the diagnostic imaging system;
   a subject support describable within the coordinate system, the subject support including reference markers able to be registered within the coordinate system;
   an x-ray sub-system, the x-ray sub-system positionable around the subject support;
   a nuclear camera sub-system including a camera head, the nuclear camera sub-system positionable around the subject support;
   means for locating the position of components of the x-ray sub-system within the coordinate system;
   means for locating the position of components of the nuclear camera sub-system within the coordinate system;
   means for locating a region of interest relative to the reference markers of the subject support; and
   means for targeting the nuclear camera head precisely at the region of interest.

10. A diagnostic imaging system, the system comprising:
    means for positioning a first imaging modality at a determined location in a coordinate system for imaging a subject;
    means for generating first image data of the subject from the first imaging modality;
    means for evaluating the first image data from the first imaging modality;
    means for identifying a region of interest in the imaged subject from the evaluated data;
    means for determining the position for the region of interest in the coordinate system from the first image data;
    means for determining a position of a nuclear camera in the coordinate system; and
    means for re-positioning the nuclear camera to image the region of interest using the determined position of the region of interest.

11. The diagnostic imaging system of claim 10 wherein the means for identifying a region of interest in the imaged subject includes means for comparing the image data from the first modality to a reference image stored in a database.

12. The diagnostic imaging system of claim 10 wherein the means for determining the position for the region of interest in a coordinate system from the first image data includes means for locating the region of interest in a three dimensional coordinate system representing a volume relating components of the imaging system.

13. A diagnostic imaging system, the system comprising:
    means for generating image data of the subject from an x-ray imaging modality;
    means for evaluating the image data from the x-ray imaging modality;
    means for identifying a region of interest in the imaged subject from the evaluated data;
    means for determining the position for the region of interest in a coordinate system from the image data; and
    means for automatically controlling positioning a nuclear camera to position the nuclear camera at the region of interest using the determined position of the region of interest.

14. A diagnostic imaging system, the system comprising:
    means for positioning a first imaging modality including an x-ray source and x-ray detector for imaging a subject;

means for generating image data of the subject from the first imaging modality;

means for evaluating the image data from the first imaging modality;

means for identifying a region of interest in the imaged subject from the evaluated data;

means for determining the position for the region of interest in the coordinate system from the image data;

means for positioning a second imaging modality including a nuclear camera detector head to image the region of interest using the determined position of the region of interest; and a positional common support member to support and positioning both of the x-ray source and nuclear camera detector head.

15. A method of targeting and imaging a region of interest in a subject, the method comprising the steps of:

positioning a first x-ray imaging modality for imaging a subject;

determining a position of the first imaging modality in a coordinate system;

generating image data of the subject from the first imaging modality;

evaluating the image data from the first imaging modality;

identifying a region of interest in the imaged subject from the evaluated data;

determining the position for the region of interest in the coordinate system from the image data;

determining a position of a nuclear camera in the coordinate system; and, positioning the nuclear camera to precisely target the region of interest using the determined positions of the region of interest and the nuclear camera.

16. The method of targeting and imaging a region of interest in a subject of claim 15 including the steps of:

detecting radiation emitted from the region of interest with the nuclear camera;

providing signals indicative of the detected radiation; and generating an image from the signals indicative of the detected radiation of the region of interest.

17. The method of targeting and imaging a region of interest in a subject of claim 15 wherein the step of identifying a region of interest in the imaged subject includes the step of comparing the image data from the first modality to a reference image stored in a database.

18. The method of targeting and imaging a region of interest in a subject of claim 15 wherein the step of positioning the nuclear camera at the region of interest is automatically controlled.

19. The method of targeting and imaging a region of interest in a subject of claim 15 wherein the step of determining the position for the region of interest in a coordinate system from the image data includes locating the region of interest in a three dimensional coordinate system representing a volume relating components of the first x-ray imaging modality and the nuclear camera.

* * * * *